United States Patent
Sato

(10) Patent No.: US 8,737,561 B2
(45) Date of Patent: May 27, 2014

(54) X-RAY PHASE GRATING AND METHOD FOR PRODUCING THE SAME

(75) Inventor: Genta Sato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 221 days.

(21) Appl. No.: 12/855,497

(22) Filed: Aug. 12, 2010

(65) Prior Publication Data

US 2011/0051889 A1 Mar. 3, 2011

(30) Foreign Application Priority Data

Aug. 26, 2009 (JP) ................. 2009-195445

(51) Int. Cl.
*G21K 1/00* (2006.01)
*A61B 6/00* (2006.01)
*G21K 1/06* (2006.01)

(52) U.S. Cl.
CPC ............... *A61B 6/484* (2013.01); *A61B 6/4291* (2013.01); *A61B 6/4035* (2013.01); *G21K 2207/005* (2013.01); *G21K 1/06* (2013.01)
USPC ........................................... 378/36; 378/149

(58) Field of Classification Search
CPC .... A61B 6/484; A61B 6/4291; A61B 6/4035; A61B 6/032; A61B 6/06; G21K 2207/005; G21K 1/06
USPC .............................. 378/36, 62, 147, 149, 154
See application file for complete search history.

(56) References Cited

U.S. PATENT DOCUMENTS

| | | | | |
|---|---|---|---|---|
| 5,812,629 A * | 9/1998 | Clauser | ............................. | 378/62 |
| 6,556,652 B1 * | 4/2003 | Mazor et al. | ..................... | 378/86 |
| 7,180,979 B2 * | 2/2007 | Momose | .......................... | 378/62 |
| 7,248,667 B2 * | 7/2007 | Weiss et al. | ...................... | 378/34 |
| 7,433,444 B2 * | 10/2008 | Baumann et al. | ............... | 378/62 |
| 7,486,770 B2 * | 2/2009 | Baumann et al. | ............... | 378/62 |
| 7,492,871 B2 * | 2/2009 | Popescu et al. | ................ | 378/145 |
| 7,522,698 B2 * | 4/2009 | Popescu et al. | ................. | 378/19 |
| 7,522,708 B2 * | 4/2009 | Heismann et al. | ............ | 378/145 |
| 7,564,941 B2 * | 7/2009 | Baumann et al. | ................ | 378/19 |
| 7,639,786 B2 * | 12/2009 | Baumann et al. | ............... | 378/145 |
| 7,746,981 B2 * | 6/2010 | Takahashi et al. | ........... | 378/98.8 |
| 7,920,673 B2 * | 4/2011 | Lanza et al. | ..................... | 378/62 |
| 7,924,973 B2 * | 4/2011 | Kottler et al. | .................... | 378/36 |
| 8,009,797 B2 * | 8/2011 | Ouchi et al. | ..................... | 378/36 |
| 8,165,270 B2 * | 4/2012 | David et al. | .................... | 378/145 |
| 2007/0183579 A1 | 8/2007 | Baumann et al. | | |

FOREIGN PATENT DOCUMENTS

| | | |
|---|---|---|
| JP | 2007-203066 A | 8/2007 |
| JP | 2008-197593 A | 8/2008 |
| JP | 2008-289878 A | 12/2008 |

* cited by examiner

*Primary Examiner* — Allen C. Ho

(74) *Attorney, Agent, or Firm* — Canon USA Inc. IP Division

(57) ABSTRACT

An X-ray phase grating used for X-ray phase-contrast imaging based on Talbot interference includes a first substrate and a second substrate. The first substrate and the second substrate are combined so as to be shifted from each other by one half period. The first substrate has a first pattern in which first faces and second faces making an angle of α (where α≠0 and α≠90°) with the first faces are periodically arranged. The second substrate has a second pattern in which third faces corresponding to the first faces and fourth faces corresponding to the second faces and making an angle of α with the third faces are periodically arranged.

20 Claims, 10 Drawing Sheets

X-RAY PHASE GRATING AND METHOD FOR PRODUCING THE SAME

BACKGROUND OF THE INVENTION

1. Field of the Invention

The present invention relates to X-ray phase gratings and methods for producing X-ray phase gratings, and particularly to an X-ray phase grating used for X-ray phase-contrast imaging based on Talbot interference and a method for producing the X-ray phase grating.

2. Description of the Related Art

X-rays are used for transmission imaging apparatuses in the fields of industry and medicine because they have high material permeability to allow examination of the internal structure of an object. X-ray phase-contrast imaging, which is promising for reducing the exposure of a subject, has recently been researched. Among others, an imaging method using Talbot interference has been theoretically possible, which uses a transmission diffraction grating to image a phase shift from interference fringes appearing under certain interference conditions. The outline of Talbot interferometry will now be described. An example of a Talbot interferometer is shown in FIG. 10A. In FIG. 10A, an X-ray source XG, a source grating SG, X-rays XR, an object O, a phase grating PG, an absorption grating AG, and a detector D are shown. Imaging by Talbot interferometry requires at least a spatially coherent X-ray source XG, a phase-modulation diffraction grating (hereinafter referred to as "phase grating") PG for periodically modulating the phase of X-rays, and a detector D. If the X-ray source XG has no coherence, the source grating SG is used to ensure spatial coherence.

Talbot interferometry using a source grating is also called Talbot-Lau interferometry. To ensure sufficient spatial coherence, it is necessary to satisfy the condition that the spatial coherence distance $\lambda \times (L/s)$ is sufficiently larger than the pitch p of the phase grating PG, where $\lambda$ is the wavelength of the X-rays XR, L is the distance between the X-ray source grating SG and the phase grating PG, and s is the size of the apertures of the X-ray source grating SG. The term "pitch" as used herein refers to the period at which grating lines or channels are arranged. In Talbot interferometry, interference fringes reflecting the shape of the phase grating PG appear at a particular distance from the phase grating PG. This is called a self-image, which appears at a distance of $(p \times p/(2\lambda)) \times n$ or $(p \times p/(8\lambda)) \times n$ from the phase grating PG, where n is an integer. This distance is called the Talbot distance d. If the object O is disposed in front of the phase grating PG, a self-image of the phase grating PG formed by the X-rays XR passing through the object O contains information about the differential phase shift of the X-rays XR due to the object O. If the absorption grating AG and the detector D are disposed at the Talbot distance d to detect the self-image, a phase image of the object O can be obtained.

A cross section of a typical phase grating PG is shown in FIG. 10B. In FIG. 10B, ridges R, slits S, the height h1 of the ridges R for phase modulation, regions r0 that cause no phase modulation, and regions r1 that cause phase modulation are shown. Typically, the amount of phase modulation is constant in the phase modulation regions r1 of the phase grating PG, the ridges R have a rectangular shape, and the cross section of the phase grating PG has a rectangular structure. For example, if 30 keV X-rays are used, the height h1 of the ridges R sufficient to cause a phase shift of $\pi$ is 38.5 µm for silicon. The pitch p, on the other hand, is often 10 µm or less in view of ensuring spatial coherence. Thus, the phase grating PG requires a small pitch and a high aspect ratio. In addition, the phase grating PG requires a large area. Furthermore, if the phase grating PG has a large area, the angle of the slits S with respect to the substrate needs to vary between the center and periphery of the phase grating PG. In the related art, for example, U.S. Patent Application No. 2007/0183579 and U.S. Pat. No. 7,639,786 propose methods for producing a rectangular structure having a high aspect ratio. According to these methods, sub-gratings having a low aspect ratio, which are easier to produce, are stacked to form an X-ray optical transmission grating having a high apparent aspect ratio.

SUMMARY OF THE INVENTION

Although the apparent aspect ratio can be increased by stacking rectangular structures having a low aspect ratio in the methods disclosed in U.S. Patent Application No. 2007/0183579 and U.S. Pat. No. 7,639,786, it has a problem in that it is difficult to produce a large-area phase grating because a wafer is used as a substrate. On the other hand, if cutting, by which a large-area phase grating can be easily produced, is used for microfabrication instead of etching using a wafer, as a substrate as in U.S. Patent Application No. 2007/0183579 and U.S. Pat. No. 7,639,786, to produce a large-area phase grating, the following problem arises in microfabrication. That is, if cutting is to be applied to form a structure as shown in U.S. Patent Application No. 2007/0183579 and U.S. Pat. No. 7,639,786, it is difficult to produce a cutting tool having a width smaller than or equal to the slit width, and it is therefore difficult to achieve a small pitch, because the rectangular slit shape involves a large contact resistance between the cutting tool and the substrate during machining.

The present invention provides an X-ray phase grating formed by cutting and used for X-ray phase-contrast imaging based on Talbot interference to obtain a high-definition X-ray phase-contrast image, and also provides a method for producing such an X-ray phase grating.

The present invention provides an X-ray phase grating and a method for producing an X-ray phase grating configured as follows. The X-ray phase grating according to the present invention is an X-ray phase grating used for X-ray phase-contrast imaging based on Talbot interference. This X-ray phase grating includes a first substrate having a first pattern in which first faces and second faces making an angle of $\alpha$ (where $\alpha \neq 0$ and $\alpha \neq 90°$) with the first faces are periodically arranged and a second substrate having a second pattern in which third faces corresponding to the first faces and fourth faces corresponding to the second faces and making an angle of $\alpha$ with the third faces are periodically arranged. The first substrate and the second substrate are combined so as to be shifted from each other by one half period so that the phase grating is capable of stepwise phase modulation. In addition, the method for producing an X-ray phase grating according to the present invention is a method for producing an X-ray phase grating used for X-ray phase-contrast imaging based on Talbot interference. This method includes the steps of forming a first pattern in which first faces and second faces making an angle of $\alpha$ (where $\alpha \neq 0$ and $\alpha \neq 90°$) with the first faces are periodically arranged on a first substrate; forming a second pattern in which third faces corresponding to the first faces and fourth faces corresponding to the second faces and making an angle of $\alpha$ with the third faces are periodically arranged on a second substrate; and combining the first substrate and the second substrate so as to be shifted from each other by one half period, thus producing a phase grating capable of stepwise phase modulation.

According to the present invention, an X-ray phase grating formed by cutting and used for X-ray phase-contrast imaging based on Talbot interference to obtain a high-definition X-ray phase-contrast image and a method for producing such an X-ray phase grating can be achieved.

Further features of the present invention will become apparent from the following description of exemplary embodiments with reference to the attached drawings.

BRIEF DESCRIPTION OF THE DRAWINGS

FIG. 1A is a sectional view of a phase grating formed by combining two serrated substrates; FIG. 1B is a sectional view of a phase grating formed by combining serrated substrates having faces parallel thereto; and FIG. 1C is a sectional view of a phase grating formed by combining serrated substrates having flat top faces.

FIG. 2A is a sectional view of a phase grating formed by combining patterned surfaces of two serrated substrates; and FIG. 2B is a sectional view of a phase grating having joint portions on the peripheries of serrated substrates.

FIG. 3A is a sectional view of a phase grating having serrated patterns on both sides of the same substrate; and FIG. 3B is a sectional view of a phase grating in which the angle between first faces and a substrate varies at different positions on the substrate.

FIG. 4A is a perspective view of serrated substrates having one-dimensional periodic patterns; FIG. 4B is a perspective view of a serrated substrate having a two-dimensional periodic pattern; and FIG. 4C is a diagram showing the X-ray phase modulation of a phase grating formed by combining two serrated substrates having two-dimensional periodic patterns.

FIG. 9A is a sectional view of a phase grating formed by stacking two substrates having serrated patterns in Examples 1 and 3; and FIG. 9B is a sectional view of a phase grating including a substrate having serrated patterns on both sides thereof in Example 2 of the present invention.

FIG. 10A is a schematic diagram showing the configuration of an X-ray Talbot interferometer; and FIG. 10B is a sectional view of a typical X-ray phase grating.

DESCRIPTION OF THE EMBODIMENTS

Figure 1A:
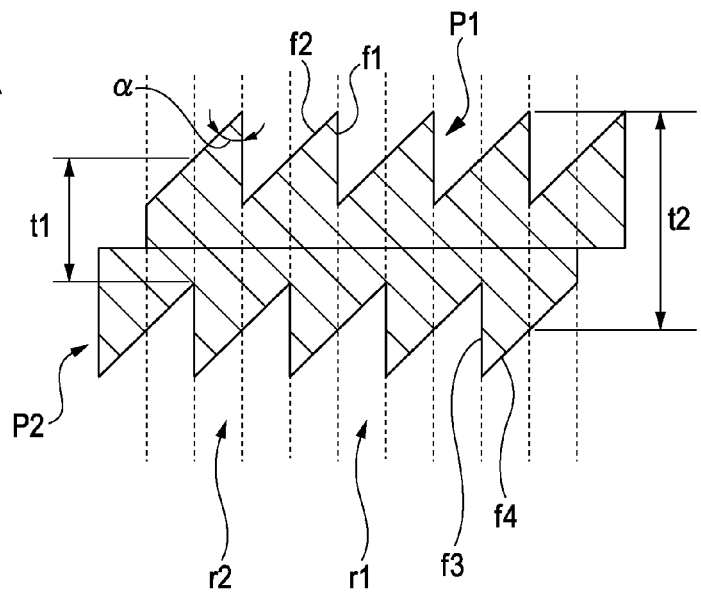
FIGS. 1A to 1C are diagrams illustrating X-ray phase gratings used for X-ray phase-contrast imaging based on Talbot interference according to an embodiment of the present invention.

X-ray phase gratings formed by combining two substrates having serrated structures according to an embodiment of the present invention will now be described with reference to the drawings. First, FIGS. 1A to 1C will be used to illustrate examples of X-ray phase gratings formed by stacking two substrates having serrated structures so as to be shifted from each other by one half period, thus having a stepwise phase modulation function equivalent to that of a rectangular structure. FIG. 1A is a sectional view showing an example of an X-ray phase grating used for X-ray phase-contrast imaging based on Talbot interference according to this embodiment. For example, a first substrate having a first pattern P1 is stacked on a second substrate having a second pattern P2. The first pattern P1 is composed only of first faces f1 and second faces f2 making an angle of $\alpha$ (where $\alpha \neq 0$ and $\alpha \neq 90°$) with the first faces f1 such that they are periodically arranged in a serrated pattern. The second pattern P2 is composed only of third faces f3 corresponding to the first faces f1 and fourth faces f4 corresponding to the second faces f2. With such serrated patterns, if the phase grating is produced by cutting, a cutting tool 2 larger than grooves can be used, and the cutting resistance can be reduced for improved machinability. On the other hand, if the phase grating is produced by injection molding, a substrate 12 can be easily released from a template 12'. When the first substrate having the first pattern P1 is stacked on the second substrate having the second pattern P2, the periodic positions of the first faces f1 are shifted from those of the third faces f3 so that thicknesses t1 and t2 in the direction normal to the substrates alternate stepwise. The first faces f1 and the third faces f3 divide the substrates into a plurality of regions in the periodic direction to form a structure in which thinner regions r1 and thicker region r2 alternate periodically. If the phase grating is produced such that the first faces f1 are parallel to the third faces f3 and the second faces f2 are parallel to the fourth faces f4, the thicknesses within the regions r1 and r2 defined between the first faces f1 and the third faces f3 are constant, for example, the thicknesses t1 and t2, respectively.

Figure 10A:
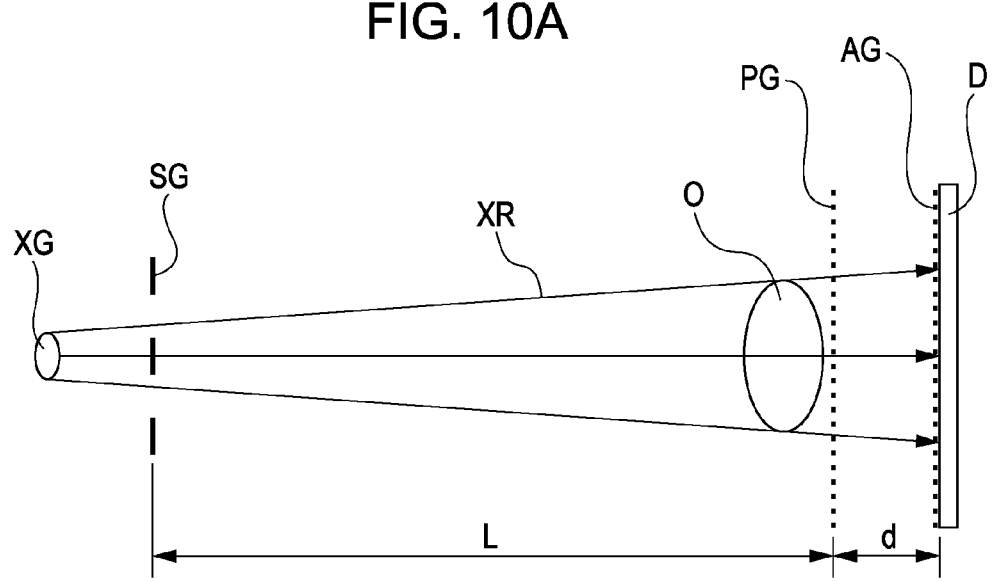
FIGS. 10A and 10B are diagrams illustrating X-ray Talbot interferometry in the related art.
Figure 10B:
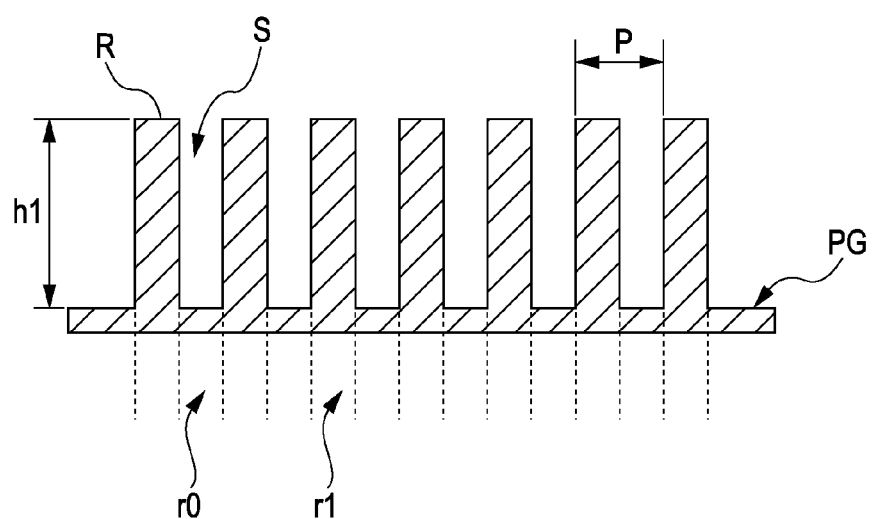

For example, if the substrates are formed of nickel, the thickness t1 is 3.1 μm, and the thickness t2 is 6.2 μm, the regions r1 having the thickness t1 cause a phase shift of $\pi$, and the regions r2 having the thickness t2 cause a phase shift of $2\pi$. The regions r2 that cause a phase shift of $2\pi$ in FIG. 1A are equivalent to the regions r0 that cause no phase shift in FIG. 10B because a phase shift of $2\pi$ is equivalent to the absence of a phase shift. Accordingly, the structures shown in FIGS. 1A and 10B are equivalent in terms of phase modulation function.

Figure 1B:
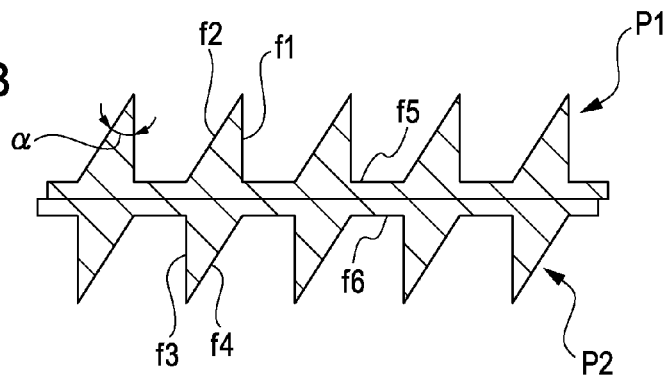

As shown in FIG. 1B, the first pattern P1 may have fifth faces f5 in addition to the first faces f1 and the second faces f2, and the second pattern P2 may have sixth faces f6 in addition to the third faces f3 and the fourth faces f4. In FIG. 1B, the fifth faces f5 and the sixth faces f6 are parallel to the plane of the substrates. Accordingly, the first pattern P1 of the first substrate includes ridges defined by the first faces f1 and the second faces f2, and the second pattern P2 of the second substrate includes ridges defined by the third faces f3 and the fourth faces f4. The first pattern P1 and the second pattern P2 are formed such that the first faces f1 are parallel to the third faces f3 and the second faces f2 are parallel to the fourth faces f4, and the first and second substrates are stacked such that the first faces f1 are shifted from the third faces f3 by one quarter period. This allows formation of regions with constant thickness surrounded by the first faces f1, the second faces f2, the third faces f3, and the fourth faces f4 and regions with constant thickness surrounded by the fifth faces f5 and the sixth faces f6, thus providing a phase grating capable of stepwise phase modulation. Thus, a phase grating can be achieved that has regions that cause a phase shift of π or less in the intensity distribution of X-rays passing through the first pattern P1 and the second pattern P2 and regions that cause a phase shift of 2π in the intensity distribution of X-rays passing through the first pattern P1 and the second pattern P2. The bottoms of the patterns P1 and P2 are defined by obtuse-angled corners and flat faces rather than by acute-angled corners, thus facilitating cutting or releasing after injection molding. A stepped phase grating may also be produced such that the thickness of the regions surrounded by the first faces f1, the second faces f2, the third faces f3, and the fourth faces f4 in the direction normal to the substrates is equal to the thickness t2 with which a phase shift of 2π occurs. Also, a phase grating may be produced such that the regions surrounded by the fifth faces f5 and the sixth faces f6 have a thickness reduced to such an extent that the phase shift is substantially zero.

Figure 1C:
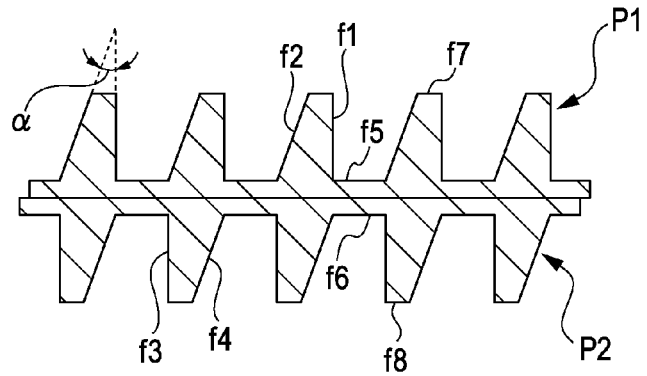

As shown in FIG. 1C, another periodic structure may be formed by replacing apices defined by the first faces f1 and the second faces f2 with seventh faces f7 and replacing apices defined by the third faces f3 and the fourth faces f4 with eighth faces f8 in the phase grating having the structure shown in FIG. 1B. In this case, the seventh faces f7 and the eighth faces f8 are parallel to each other and have the same length in the periodic direction.

Figure 2A:
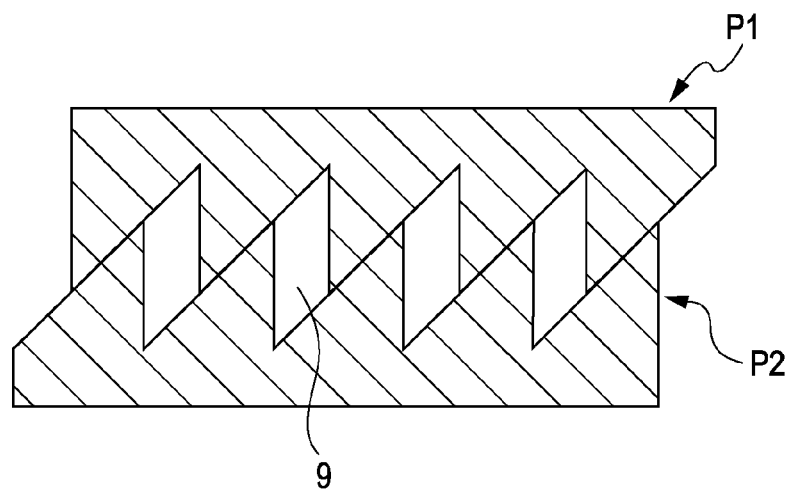
FIGS. 2A and 2B are diagrams illustrating X-ray phase gratings used for X-ray phase-contrast imaging based on Talbot interference according to an embodiment of the present invention.

The first substrate having the first pattern P1 may be stacked on the second substrate having the second pattern P2 such that unpatterned surfaces thereof face each other, as shown in FIG. 1A, or such that patterned surfaces thereof faces each other, as shown in FIG. 2A. If the patterned surfaces face each other, the first pattern P1 and the second pattern P2 may be either partially in contact with or separated from each other. If the substrates are stacked such that the patterned surfaces thereof face each other, flat surfaces are externally exposed, so that the fine patterns can be prevented from being damaged when hit by another member. The first pattern P1 and the second pattern P2 may be formed either on different substrates or on the same substrate. If the first pattern P1 and the second pattern P2 are formed on different substrates, regions 9 between the patterns P1 and P2 may be filled with a material having a different refractive index from the material forming the patterns P1 and P2. For example, if the surface having the first pattern P1 and the surface having the second pattern P2 are stacked by filling the regions 9 with a material such as resin, no voids are formed between the first pattern P1 and the second pattern P2, thus increasing the strength of the substrates. The first substrate having the first pattern P1 and the second substrate having the second pattern P2 may have joint portions 10 and 14, respectively.

Figure 2B:
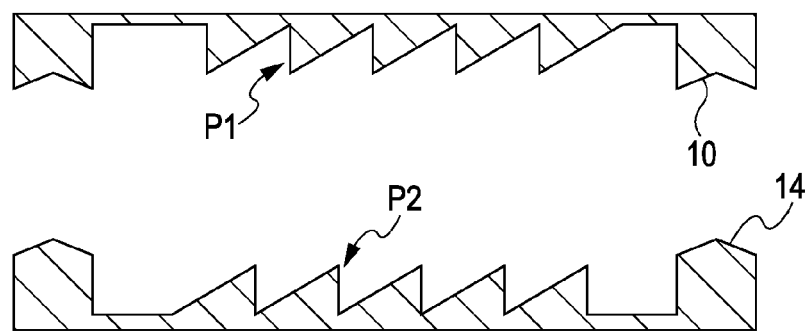
Figure 3A:
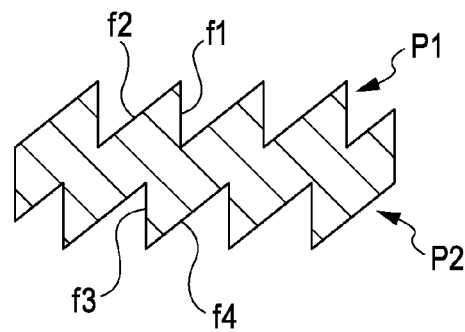
FIGS. 3A and 3B are diagrams illustrating X-ray phase gratings used for X-ray phase-contrast imaging based on Talbot interference according to an embodiment of the present invention.

FIG. 2B shows a sectional view of substrates having joint portions. For example, the substrate having the first pattern P1 has a recessed joint portion 10, and the substrate having the second pattern P2 has a raised joint portion 14. These joint portions 10 and 14 are formed at the same time as the formation of the first pattern P1 and the second pattern P2 so that their positional relationship can be accurately determined. Thus, if the first substrate having the first pattern P1 and the second substrate having the second pattern P2 are joined at the joint portions 10 and 14, the first pattern P1 and the second pattern P2 can be combined with the desired positional relationship. As shown in FIG. 3A, the first pattern P1 and the second pattern P2 may be formed on either side of the same substrate. If the first pattern P1 and the second pattern P2 are formed on the same substrate, their positional relationship can be accurately determined during machining. In addition, a stacking step can be eliminated.

Figure 3B:
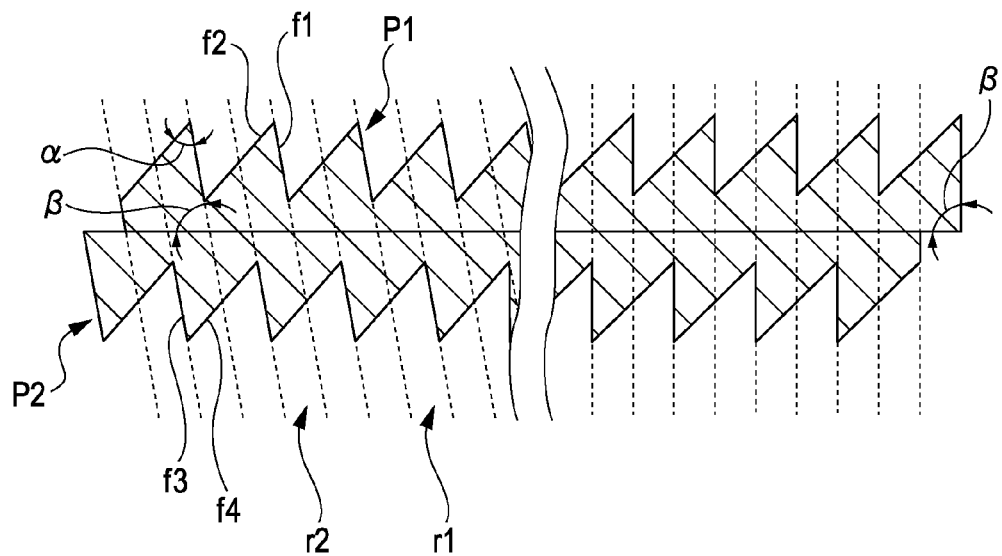

As shown in FIG. 3B, the angle β between the first faces f1, which are periodically arranged, and the plane of the substrate having the first faces f1 may vary in the plane of the substrate. In addition, the angle β between the third faces f3 and the plane of the substrate having the third faces f3 may vary in the plane of the substrate. In Talbot interferometry, parallel light, such as synchrotron radiation, or diverging light, such as that from an X-ray tube, is used as an X-ray source. If diverging light passes through the phase grating, the angle between the propagation direction of the X-rays and the plane of the substrates of the phase grating varies at different positions in the plane of the phase grating. Specifically, the propagation direction of the X-rays and the plane of the substrates make a substantially right angle (substantially 90°) in the center of the phase grating and make an angle of less than 90° at a position away from the center of the phase grating toward the periphery thereof. For example, if X-rays generated at a position 2 m away from the substrates propagate in the direction normal to the substrates (in the 90° direction) in the center of the substrates, the propagation direction of the X-rays is shifted by 1°, namely, 89°, at a peripheral position 35 mm away from the center of the substrates. A phase grating applied to Talbot interferometry using diverging light is formed by adjusting the angle β between the first faces f1 and the third faces f3 and the plane of the substrates depending on the propagation direction of the X-rays. Accordingly, the angles of the individual faces f1 and f3 are set such that the angle between the first faces f1 and the third faces f3 and the plane of the substrates decreases from the center to the periphery of the phase grating. For example, a phase grating suitable for the X-ray source described above can be designed so that the angle β is 90° in the center and is (90-arctan(x/2)) degrees at a peripheral position x. This allows a constant amount of phase modulation to be maintained in the plane of the phase grating for X-rays obliquely incident on the plane of the substrates. A phase grating supporting diverging light can also be formed with a constant angle β between the first faces f1 and the plane of the substrate having the first faces f1 by bending the substrates.

Figure 4A:
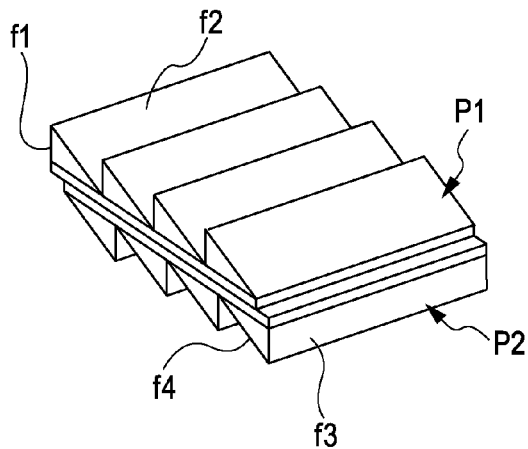
FIGS. 4A to 4C are perspective views of X-ray phase gratings including serrated substrates.
Figure 4B:
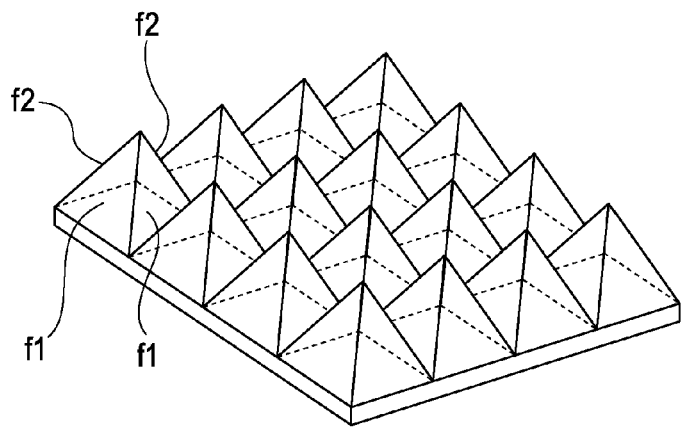
Figure 4C:
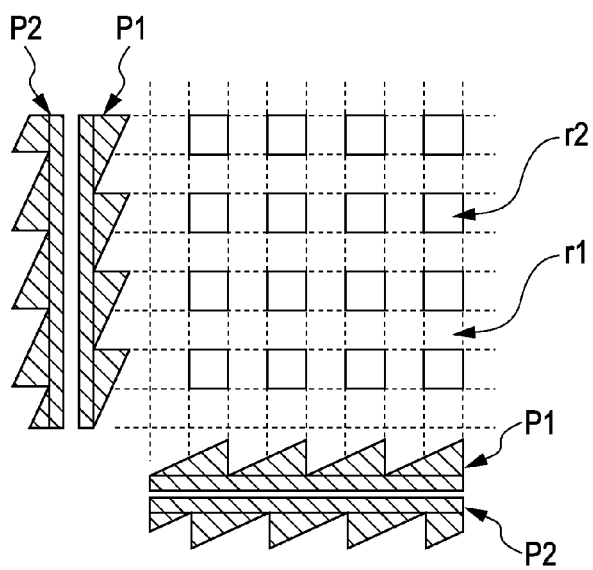
Figure 5A:
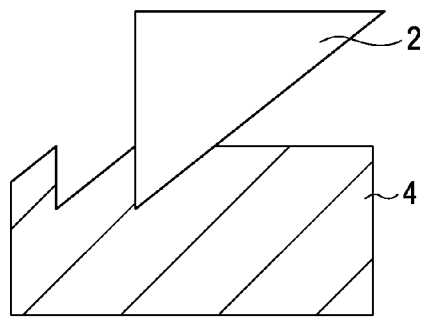
FIGS. 5A to 5E are diagrams illustrating a process of forming a substrate having a serrated pattern by cutting in an embodiment of the present invention.
Figure 5D:
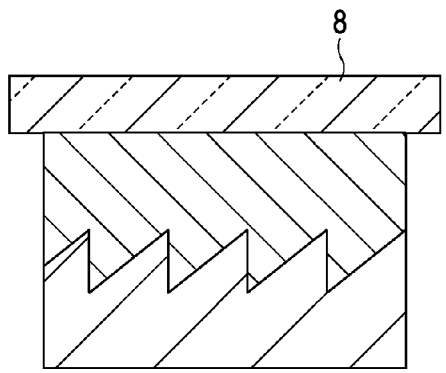
Figure 5B:
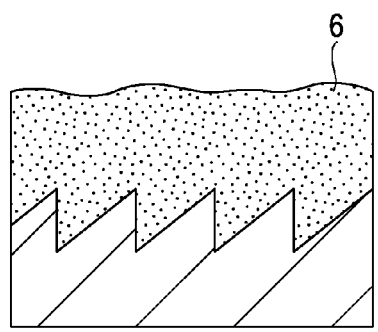
Figure 5E:
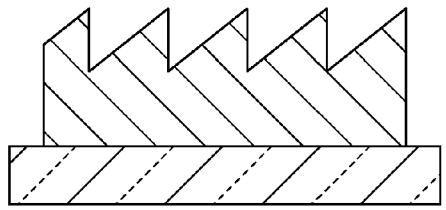
Figure 5C:
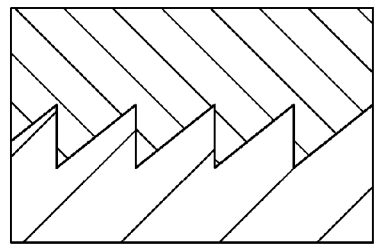
Figure 6A:
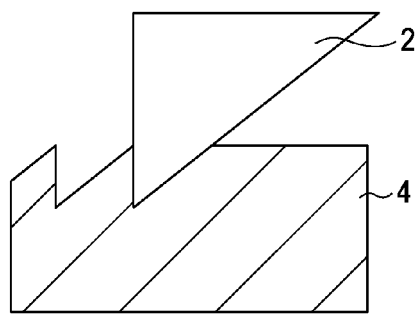
FIGS. 6A to 6E are diagrams illustrating a process of forming a substrate having serrated patterns on both sides thereof in an embodiment of the present invention.
Figure 6D:
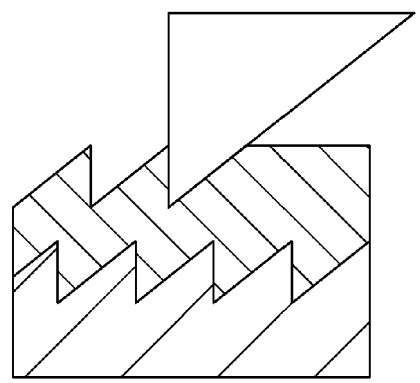
Figure 6B:
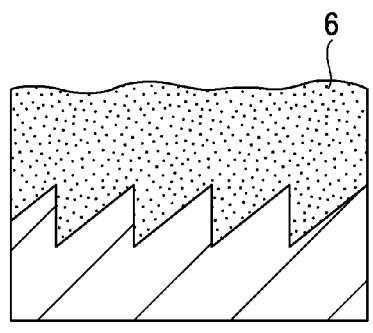
Figure 6E:
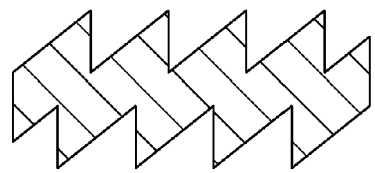
Figure 6C:
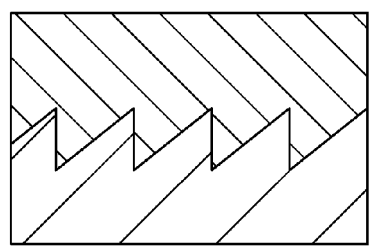
Figure 7A:
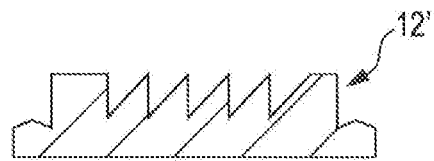
FIGS. 7A to 7D are diagrams illustrating a process of forming a substrate having a serrated pattern by injection molding in an embodiment of the present invention.
Figure 7B:
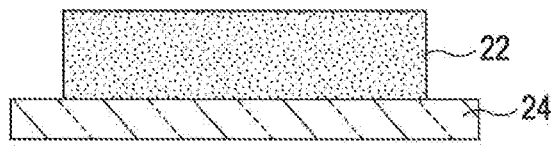
Figure 7C:
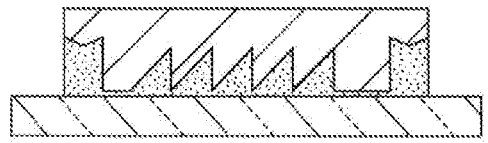
Figure 7D:
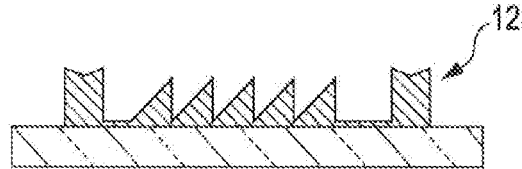
Figure 8A:
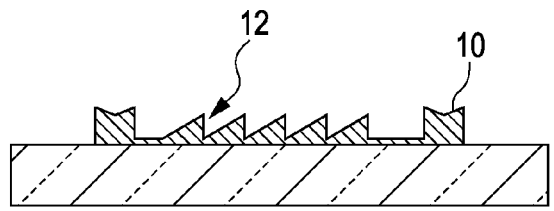
FIGS. 8A to 8D are diagrams illustrating a process of stacking two substrates having serrated patterns in Example 1 of the present invention.
Figure 8B:
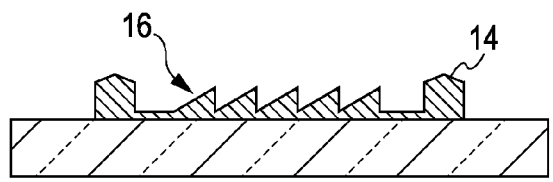
Figure 8C:
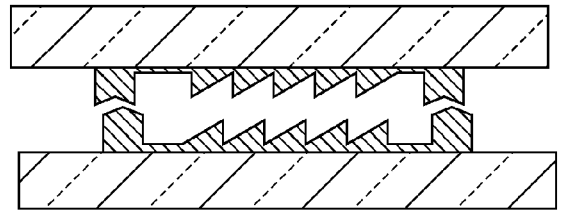
Figure 8D:
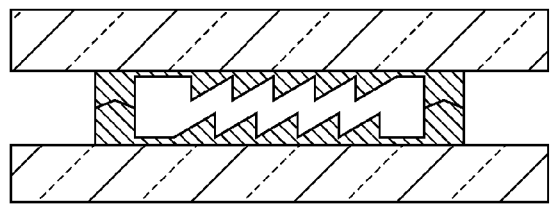

In addition, the first pattern P1 and the second pattern P2 may be formed in one dimension, as shown in FIG. 4A, or may be formed in two dimensions, as shown in FIG. 4B. If first and second substrates having first and second two-dimensional patterns P1 and P2 are stacked, as shown in FIG. 4C, the first and second patterns P1 and P2 are formed so as to be shifted from each other by, for example, one half period in each of the vertical and horizontal directions. This allows formation of a two-dimensional phase grating having a dot pattern of regions r2 that cause a phase shift of 2π and a grid pattern of regions r1 that cause a phase shift of π. The phase grating may be formed of a metal such as nickel or copper or a resin such as polycarbonate (PC), polyimide (PI), poly (methyl methacrylate) (PMMA), or a photoresist. In the phase grating, the thickness of the portion that absorbs X-rays without contributing to phase modulation can be reduced. In this case, the phase grating may be bonded to a substrate that absorbs little X-rays, such as a glass or silicon substrate, as a support.

To produce the phase grating, various techniques can be used, including cutting; photolithography; dry etching; various deposition processes such as sputtering, evaporation, CVD, electroless plating, and electrolytic plating; injection molding; and nanoimprinting. For example, as shown in FIGS. 5A to 5E, the phase grating can be produced by preparing a template by cutting, depositing a nickel film by plating, and transferring it onto a support substrate 8. In FIGS. 5A to 5E, a cutting tool 2, a cutting original 4, a phase grating material 6, and the support substrate 8 are shown. The joint portions 10 and 14 are formed if substrates are stacked. The shapes of the joint portions 10 and 14 can be sharp so that the substrates can be stacked by self-alignment. Alternatively, as shown in FIGS. 6A to 6E, a phase grating having patterns on both sides of the same substrate can be produced by performing cutting again after the deposition. Also, as shown in FIGS. 7A to 7D, a substrate or a material 22 deposited on a substrate may be subjected to injection molding using a template 12' prepared by cutting. In FIGS. 7A to 7D, a substrate 12 having a serrated pattern, a template 12' for transferring the serrated pattern, and a substrate 24 for supporting a material onto which the serrated pattern is to be transferred are shown.

EXAMPLES

Examples of the present invention will now be described.

Example 1

Figure 9A:
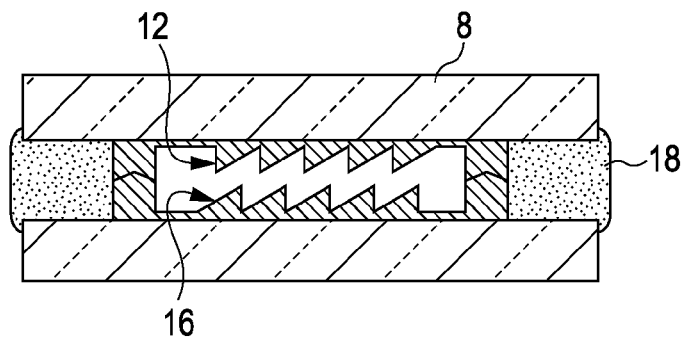
FIGS. 9A and 9B are diagrams illustrating methods for producing X-ray phase gratings in examples of the present invention.

In Example 1, an example of a method for producing a phase grating by combining two substrates, each having a serrated structure on one surface thereof, so that the serrated surfaces are shifted from each other by one half period to achieve stepwise phase modulation will be described. An oxygen-free copper substrate 4 is subjected to cutting using a cutting tool 2 having an edge angle of 45° to form a substrate 12 having a serrated pattern having a pitch p of 3.1 μm and a depth of 3.1 μm and including a joint portion 10. A nickel film 6 is then deposited on the oxygen-free copper substrate 4 by nickel plating and is polished to a thickness of 6.15 μm. Subsequently, the polished surface is bonded to a glass support substrate 8, and the oxygen-free copper substrate 4 is removed by dissolution (see FIGS. 5A to 5E). Similarly, a substrate 16 having a second serrated pattern formed so as to be shifted by one half period and including a joint portion 14 is prepared, and the two substrates are stacked with the patterned surfaces thereof facing each other (see FIGS. 8A to 8D). Subsequently, voids are evacuated to a vacuum from end surfaces of the glass substrate 8 and are sealed with a resin adhesive 18 (see FIG. 9A). Thus, a phase grating that causes a phase shift of $\pi/2$ for 17.4 keV X-rays is obtained.

Example 2

Figure 9B:
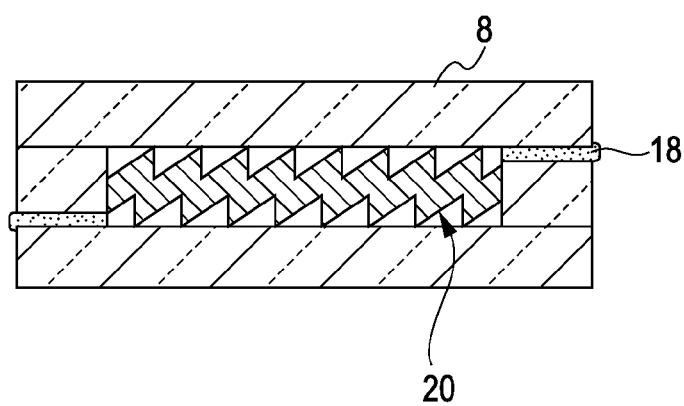

In Example 2, an example of a method for producing a phase grating by forming serrated structures on both surfaces of a substrate such that they are shifted from each other by one half period to achieve stepwise phase modulation will be described. A nickel film 6 is deposited on an oxygen-free copper substrate 4 subjected to cutting as in Example 1 by nickel plating, and the same serrated pattern as that of the oxygen-free copper substrate 4 is formed on the nickel film 6 such that they are shifted by one half period, where the thickest portion has a thickness of 12.3 μm. After the oxygen-free copper substrate 4 is removed by dissolution, the nickel film 6 is covered and sealed with resin support substrates 8. Thus, a phase grating that causes a phase shift of $\pi/2$ for 17.4 keV X-rays is obtained (see FIG. 9B). In FIG. 9B, a substrate 20 having a first pattern and a second pattern on either side thereof is shown.

Example 3

In Example 3, another example of a method for producing a phase grating by combining two substrates, each having a serrated structure on one surface thereof, so that the serrated surfaces are shifted from each other by one half period to achieve stepwise phase modulation will be described. As in Example 1, the oxygen-free copper substrate 4 is subjected to cutting to form a structure 12' complementary to a serrated pattern having a pitch of 11.1 μm and a depth of 11.1 μm. As the transfer material 22, an SU-8 photoresist manufactured by Kayaku Microchem Corporation is applied to a glass substrate 24, and the template pattern is transferred thereto by injection molding.

After the photoresist is cured by ultraviolet irradiation through the glass substrate 24, the template is removed. Thus, the serrated pattern including the joint portion 10 is obtained (see FIGS. 7A to 7D). In the removal step, the serrated template is advantageous over a rectangular template in that the serrated template can be more easily removed. Two resin substrates thus formed are stacked and sealed. Thus, a phase grating that causes a phase shift of $\pi/2$ for 17.4 keV X-rays is obtained (see FIG. 9A).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-195445 filed Aug. 26, 2009, which is hereby incorporated by reference herein in its entirety.

What is claimed is:

1. An X-ray phase grating used for X-ray phase-contrast imaging based on Talbot interference, comprising:
   a first substrate having a first pattern in which first faces and second faces making an angle of $\alpha$ with the first faces are periodically arranged, where $\alpha \neq 0$ and $\alpha \neq 90°$; and
   a second substrate having a second pattern in which third faces and fourth faces making an angle of $\alpha$ with the third faces are periodically arranged;
   wherein the first substrate and the second substrate are configured integrally with each other,
   wherein the second pattern has a same period as the first pattern, and
   wherein the first pattern and the second pattern are combined so as to be shifted from each other.

2. The X-ray phase grating according to claim 1, wherein the first faces are parallel to the third faces, and the second faces are parallel to the fourth faces.

3. The X-ray phase grating according to claim 1, wherein the first pattern and the second pattern are formed on different substrates.

4. The X-ray phase grating according to claim 3, wherein a region between the first pattern and the second pattern is filled with a material having a different refractive index from a material forming the first and second patterns.

5. The X-ray phase grating according to claim 1, wherein the first substrate and the second substrate are the same substrate, and the first pattern and the second pattern are formed on opposing sides of the same substrate.

6. The X-ray phase grating according to claim 1, wherein the angle between the first faces and the plane of the substrate having the first faces decreases from the center to the periphery of the first substrate, and the angle between the third faces and the plane of the substrate having the third faces decreases from the center to the periphery of the second substrate.

7. The X-ray phase grating according to claim 1, wherein the first pattern and the second pattern are formed in two dimensions.

8. The X-ray phase grating according to claim 1,
wherein the first pattern and the second pattern are shifted from each other by one half period of the first pattern and the second pattern.

9. The X-ray phase grating according to claim 1,
wherein a shape of the second pattern is the same as a shape of the first pattern, and
wherein the third faces correspond to the first faces and the fourth faces correspond to the second faces.

10. An X-ray phase grating used for X-ray phase-contrast imaging based on Talbot interference, comprising:
a first substrate having a first pattern in which first faces and second faces making an angle of $\alpha$ with the first faces are periodically arranged, where $\alpha \neq 0$ and $\alpha \neq 90°$; and
a second substrate having a second pattern in which third faces and fourth faces making an angle of $\alpha$ with the third faces are periodically arranged;
wherein the first pattern and the second pattern are combined so as to be shifted from each other,
wherein the first pattern and the second pattern are formed on different substrates, and
wherein the first substrate having the first pattern and the second substrate having the second pattern have joint portions for joining the substrates.

11. The X-ray phase grating according to claim 10,
wherein the second pattern has a same period as the first pattern.

12. The X-ray phase grating according to claim 11,
wherein the first pattern and the second pattern are shifted from each other by one half period of the first pattern and the second pattern.

13. The X-ray phase grating according to claim 10,
wherein the first pattern and the second pattern are shifted from each other by one half period of the first pattern and the second pattern.

14. An X-ray phase grating used for X-ray phase-contrast imaging based on Talbot interference, comprising:
a first substrate having a first pattern in which first faces and second faces making an angle of $\alpha$ with the first faces are periodically arranged, where $\alpha \neq 0$ and $\alpha \neq 90°$; and
a second substrate having a second pattern in which third faces and fourth faces making an angle of $\alpha$ with the third faces are periodically arranged;
wherein the first pattern and the second pattern are combined so as to be shifted from each other,
wherein the first pattern and the second pattern are formed on different substrates, and
wherein the first substrate is in contact with the second substrate.

15. The X-ray phase grating according to claim 14,
wherein the second pattern has a same period as the first pattern.

16. The X-ray phase grating according to claim 14,
wherein the first pattern is in contact with the second pattern.

17. The X-ray phase grating according to claim 14,
wherein a face, of the first substrate, opposing to a face on which the first pattern is formed is in contact with a face, of the second substrate, opposing to a face on which the second pattern is formed.

18. A Talbot interferometer comprising:
the X-ray phase grating according to claim 1, and
a detector detecting interference fringes reflecting a shape of the X-ray phase grating.

19. A Talbot interferometer comprising:
the X-ray phase grating according to claim 10, and
a detector detecting interference fringes reflecting a shape of the X-ray phase grating.

20. A Talbot interferometer comprising:
the X-ray phase grating according to claim 11, and
a detector detecting interference fringes reflecting a shape of the X-ray phase grating.

* * * * *